(12) United States Patent
King et al.

(10) Patent No.: US 8,075,184 B2
(45) Date of Patent: Dec. 13, 2011

(54) X-RAY CALIBRATION

(76) Inventors: Richard King, Solihull (GB); Damain Griffin, Warwick (GB)

( * ) Notice: Subject to any disclaimer, the term of this patent is extended or adjusted under 35 U.S.C. 154(b) by 62 days.

(21) Appl. No.: 12/626,212

(22) Filed: Nov. 25, 2009

(65) Prior Publication Data

US 2010/0135467 A1 Jun. 3, 2010

(30) Foreign Application Priority Data

Nov. 26, 2008 (GB) .................................. 0821635.0
Aug. 21, 2009 (GB) .................................. 0914695.2

(51) Int. Cl.
*G01D 18/00* (2006.01)
(52) U.S. Cl. ....................... 378/207; 378/205
(58) Field of Classification Search .................. 378/207, 378/163, 205–206
See application file for complete search history.

(56) References Cited

U.S. PATENT DOCUMENTS

| | | | | |
|---|---|---|---|---|
| 5,970,119 | A * | 10/1999 | Hofmann | 378/163 |
| 6,459,772 | B1 | 10/2002 | Wiedenhoeffer | |
| 6,473,489 | B2 * | 10/2002 | Bani-Hashemi et al. | 378/63 |
| 2004/0252811 | A1 | 12/2004 | Morita | |
| 2006/0115054 | A1 | 6/2006 | Yatsenko | |
| 2009/0268865 | A1 * | 10/2009 | Ren et al. | 378/37 |

FOREIGN PATENT DOCUMENTS

| | | |
|---|---|---|
| EP | 1880672 | 1/2008 |
| WO | WO2008016796 | 2/2008 |

\* cited by examiner

*Primary Examiner* — Hoon Song
(74) *Attorney, Agent, or Firm* — Ice Miller LLP

(57) ABSTRACT

Methods, devices, and kits for determining the magnification of an x-ray image of an object, or a portion of an object are described. An exemplary method comprises the steps of providing an object to be x-rayed, providing a first posterior x-ray marker having a pre-determined dimension, providing anteriorly to the object to be x-rayed, a second x-ray marker having predetermined dimensions, recording an x-ray image of the object, the first posterior x-ray marker, and second x-ray markers, and comparing a dimension of the first posterior x-ray marker recorded on the x-ray image, and a dimension of the second x-ray marker recorded on the image to a pre-determined value for the object x-rayed, to estimate a magnification of the x-ray image of the object.

20 Claims, 11 Drawing Sheets

X-RAY CALIBRATION

The present application is related to, and claims the priority benefit of, Great Britain Patent Application Serial No. 0914695.2, filed Aug. 21, 2009, which is related to, and claims the priority benefit of, Great Britain Patent Application Serial No. 0821635.0, filed Nov. 26, 2008. The contents of each of these applications are hereby incorporated by reference in their entirety into this disclosure.

The invention relates to a method and apparatus for identifying the magnification of the x-ray image of an object. Such a device and method is particularly useful for calibrating x-ray images where the size of a particular feature, for example the size of a limb socket, such as a hip socket, needs to be accurately determined to allow the assessment of replacement parts, such as hip replacements.

X-ray imaging of objects has been carried out for many years. Until fairly recently the capture of an x-ray image has been carried out using an x-ray film. This has meant that the variability of the size of the image captured by the x-ray film has been reasonably consistent. However, the more recent use of digital x-ray capture, where the x-ray image is captured digitally and stored as a digital image, has meant that the size of an image presented to a practitioner may vary considerably depending upon, for example, the computer screen displaying the image. There are many situations where the size of the object displayed on the image needs to be accurately calibrated. For example, in surgical operations where a joint, such as a hip or other joint, is replaced.

Bayne et al (J. Arthoplasty 2008) discloses evaluation of the accuracy of x-ray markers in digital templating of total hip arthoplasty. This shows that measurement of hips via digital images of x-rays is currently inaccurate and variable. Such markers are often uncomfortable for the patient as they often need to be positioned between the thighs of a patient, which is often felt to be intrusive. Adhesive markers have also been used. If the marker is not positioned accurately, then the size of the marker is misread on the x-ray and the magnification mis-calculated. The paper recommends positioning the marker at the lateral trochanter to improve accuracy. However, this procedure is prone to errors as it requires accurate positioning of the marker.

The et al (J. Digital Imaging 2007, 329-335) also looked at calibration of hip x-rays. This produced a prediction equation to predict height of the hip socket centre to correct magnification of pelvic x-rays. The predictor utilised a number of variables including pelvic width and abdominal circumference to evaluate the distance of the hip above a table. This is a complicated method to follow.

The inventors of the current application have reviewed x-ray images of hips taken over a range of patients. Such images should conventionally have a marker ball of a pre-determined size accurately positioned to allow the size of the hip joint to be accurately calibrated. In some 40% of cases, it was impossible to know what the actual magnification of the x-ray image was. This was due to either markers being missed from the image or, alternatively, from poor positioning of the markers. One problem that was apparent from the work carried out by the inventors was that it was often difficult for x-ray radiographers to accurately assess where to position the marker ball in patients, especially where they were particularly obese.

Inaccurate measurement of the size of hip joints or other joint can lead to the incorrect size of replacement sockets being made available, potentially leading to either operations being cancelled or, alternatively, the incorrect size of replacement sockets being implanted.

FIG. 1 shows a schematic representation of a typical x-ray arrangement. The oval 10, represents a cross-section through the pelvis of a patient, with the hip sockets represented by circles 12. The patient lies upon a mattress 14, which is placed against an x-ray detector 16. X-rays are provided from an x-ray source 18. X-rays spread out from the x-ray source, 18, as represented by the divergent lines 20. This means that any image captured by the x-ray detector is not an exact representation of the true size of the object placed upon the mat 14. Moreover, the size of the image will vary depending on how it is represented on a computer screen. To overcome this it has been conventional to place a marker 22 made of a substantially x-ray opaque material, such as steel, level with the plane of the hips, represented by line 24. This requires accurate positioning of the marker.

The calibration system proposed by the inventors is a dual marker system that is easier to use by the x-ray radiographer and at the same time improves the accuracy of the determination of the magnification of the object receiving the x-ray. The inventors also realised that using multiple markers would improve the chance of the markers actually being present on the x-ray. Moreover, the relationship between the markers now identified by the inventors has allowed accuracy to be improved.

The first aspect of the invention provides a method of determining the magnification of an x-ray image of an object, or a portion of an object, comprising:
(i) providing the object to be x-rayed;
(ii) providing a first posterior x-ray marker having pre-determined dimensions;
(iii) providing anteriorly to the object to be x-rayed a second x-ray marker having pre-determined dimensions;
(iv) recording an x-ray image of the object and the first and second x-ray markers; and
(v) comparing a dimension of the first x-ray marker recorded on the image and a dimension of the second x-ray marker recorded on the image to a pre-determined value for the object x-rayed, to estimate the magnification of the image of the object.

Typically, the pre-determined value for the object is a pre-determined comparative value representing (i) the average distance between a point on or within the object, or portion of the object, and the position of either the first x-ray marker or the second x-ray marker when used with the object, compared to (ii) the average total distance between the first x-ray marker and second x-ray marker on a typical object or portion of the object. This is typically represented as a ratio between the two values.

The average distances may be predetermined by measuring the distances on a number of different objects, such as patients, to produce the average distances.

FIG. 2 shows an example of an arrangement according to the invention. The example uses the position of the hip sockets in a patient. However, the same principles may also equally apply to other objects to other parts of a human or animal.

In FIG. 2 the first posterior marker 30, is placed behind a patient 10, at the side away from the x-ray source 18. A second marker (the anterior marker) 32, is placed upon the abdomen of the patient 10, closest to the x-ray source 18. The distance between the markers 30 and 32 is shown by "d". The typical distance between a plane 24, through the hip sockets 12, to the surface of the abdomen where the anterior marker 32, was placed was assessed on transverse slices through patients taken on CT scans. This allows the average ratio between the distance between the plane 24, and the abdomen ("R") compared to the total distance d to be determined.

FIG. 3 shows a schematic representation of an x-ray taken of the arrangement shown in FIG. 2. Because the x-rays diverge from the x-ray source 18, the size of the markers 30 and 32 will vary depending on the relative position of the two markers. An image of the anterior marker 32 recorded by the x-ray detector 16 will have greater magnification than the posterior marker 30. This is because the anterior marker 32 is closer to the x-ray source 18 and will cast a greater "shadow". The size of the two images are represented by "$X_p$" for the posterior marker and "$X_a$" for the anterior marker in FIG. 3. Knowing the positions of the two markers relative to one another, because of the predetermined value (the ratio R), allows the relative magnification of the image to be determined.

Preferably, the magnification is determined for a predetermined point within the object or portion of the object to be magnified. Hence, the magnification may be determined by the equation $$M = \frac{100}{\left[\frac{S_a}{X_a}\right] + R\left[\frac{S_p}{X_p} - \frac{S_a}{X_a}\right]}$$

where,
M is the magnification,
$S_a$ is the actual dimension of the anterior marker,
$S_p$ is the actual dimension of the posterior marker,
$X_a$ is the apparent dimension of the anterior marker recorded on the image,
$X_p$ is the apparent dimension of the posterior marker recorded on the image and
R is the pre-determined value.

As indicated above, R is typically the ratio between a relative point within the object, such as the plane of the hips, to the position of the anterior marker, compared to the distance between the anterior marker and the posterior marker.

The x-ray markers are typically substantially x-ray opaque to allow them to be detected on the x-ray detector. They may be any shape, including disc shaped, rectangular, rod shaped, wires and balls. The material that the markers are made of may, for example, be steel. Ball shaped markers, such as ball-bearings are especially preferred for the anterior markers. This is if the ball-bearing is placed on a slight slant, for example on the abdomen of a patient, the apparent size of the marker will be consistent as the x-ray passing through the ball will produce a consistent circular marker shape, the diameter of which can be readily determined. Other shapes placed at an angle may distort, as they may not be placed perpendicular to the x-ray beam. The pre-determined dimension may be, for example, the diameter of the ball and its circular image, or the length of a rod. However, for example, two parallel wires may be used. The pre-determined dimension may be the distance between the two wires or their image. Such rods and wires may be used when the markers are perpendicular to the x-ray beam. A disc or preferably a circular ring of material such as a washer may also be used. The latter has some advantage because they do not obscure the x-ray as much as a ball.

Typically, the object is a human or animal patient. However, this technique may also be applied to the calibration of other objects. The first x-ray marker is typically provided substantially adjacent to an x-ray detector. For example, this may be placed on or recessed into a mat on which the patient lies. The mat is placed upon the x-ray detector. The marker may be a disposable. It may be tape. It may comprise a radioopaque marker, such as parallel wires or radioopaque lettering of predetermined size. The tape may comprise an adhesive backing to attach the tape to a surface on which the patient lies.

The second x-ray marker may be placed upon the surface of the object to be x-rayed anteriorly to the x-ray source. For example, this may be the abdomen of the patient. The portion of human or animal body selected may, for example, be a hip joint, a knee joint, a shoulder joint, an elbow or a portion of the spinal column. The portion of the object x-rayed may be a human hip joint and a predetermined value is the typical ratio of the distance between a line passing through the centres of both hip joints of a typical patient to the position of the anterior marker if placed on the surface of the abdomen, compared to the distance between the anterior marker and posterior marker.

The object may be placed on a mat adjacent to an x-ray detector, the mat comprising one or more markers. Alternatively a tape, such as a disposable tape, comprising one or more markers may be placed on a surface on which the object is placed. The tape may comprise an adhesive to attach it to the surface.

Preferably, the anterior marker is one or more balls or one or more radioopaque discs or washers. The anterior marker may be disposable. It may comprise a plurality of markers, such as washers or discs on a flexible material, which may be a tape, such as a cloth or plastics material.

A further aspect of the invention provides a kit for use in the method according to any preceding claim comprising a tape or mat, the tape or mat comprising one or more markers, the markers having a predetermined dimension and capable of being detected by x-ray imaging. The markers may be selected from rods or wires, which may be recessed into the surface of the tape or mat or be within the tape or mat. The rest of the mat may, for example, be made of a foam material covered with a plastics material. The wires or rods may be parallel to one another.

Additionally, the kit may comprise one or more ball-bearings discs or washers for placing on an anterior surface of the object to be x-rayed. The ball-bearings discs or washers may be linked together by one or more strips of flexible material, such as a cloth or plastics material.

A further aspect of the invention provides an x-ray source, an x-ray detector and a kit according to the invention.

A still further aspect of the invention provides a computer program product comprising instructions, which when run on a computer, provide or perform the following method:
(i) Calculate a dimension of an image representing a first posterior x-ray marker and a dimension of an image of a second anterior x-ray marker; and
(ii) Comparing the two dimensions calculated in step (i) with a pre-determined value of an object or part of an object, the x-ray image of which is also present with the image of the first and second x-ray markers, to provide an estimated magnification of the image of the object or part of the object.

A still further aspect of the invention provides a computer comprising a processor and a memory, the memory comprising an image, the image comprising an image of a first x-ray marker and an image of a second x-ray marker and an image of an object or part of an object, the computer configured to:
(i) place a cursor over the image of the first x-ray marker and calculate a dimension of it;
(ii) place a cursor over the image of the second x-ray marker and calculate a dimension of it; and
(iii) compare the two dimensions with a pre-determined value for the object, or part of the object, to provide an estimate of the magnification of the image.

The memory, may, for example, be RAM, Flash Memory or other computer memory. The computer may run a program according to a previous aspect of the invention. The computer program product or computer according to the invention may estimate the magnification of the image using the following equation:

$$M = \frac{100}{\left[\frac{S_a}{X_a}\right] + R\left[\frac{S_p}{X_p} - \frac{S_a}{X_a}\right]}$$

where,
M is the magnification,
$S_a$ is the actual dimension of the anterior marker,
$S_p$ is the actual dimension of the posterior marker,
$X_a$ is the apparent dimension of the anterior marker recorded on the image,
$X_p$ is the apparent dimension of the posterior marker recorded on the image and
R is the pre-determined value.

The object, x-ray markers, dimensions, predetermined value etc, may be according to any preceding aspect of the invention, The invention will now be described by way of example only with reference to the following figures.

Figure 1:
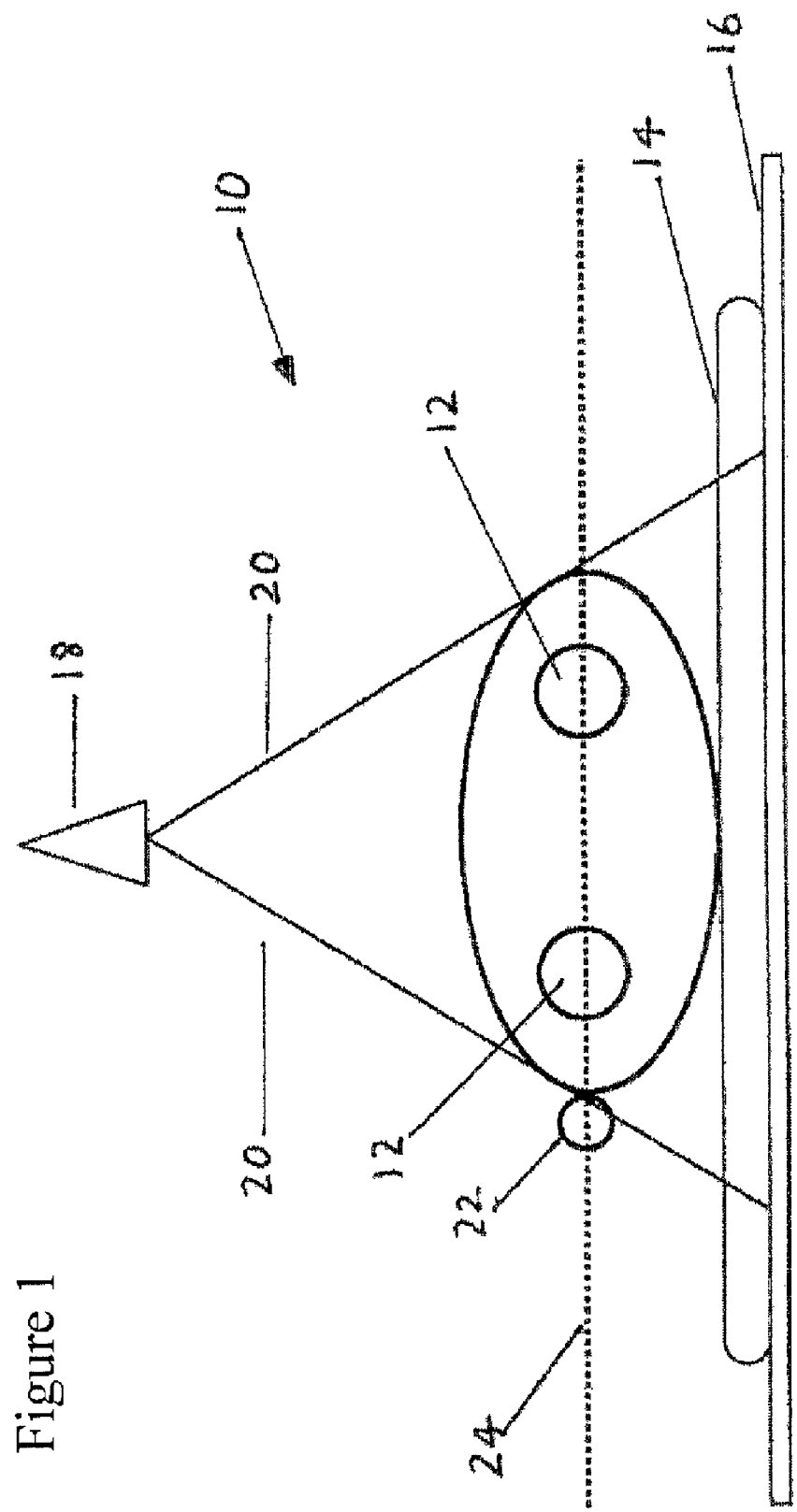
FIG. 1 shows a schematic diagram of a cross-section through a patient having an x-ray taken using a prior art marker.
Figure 2:
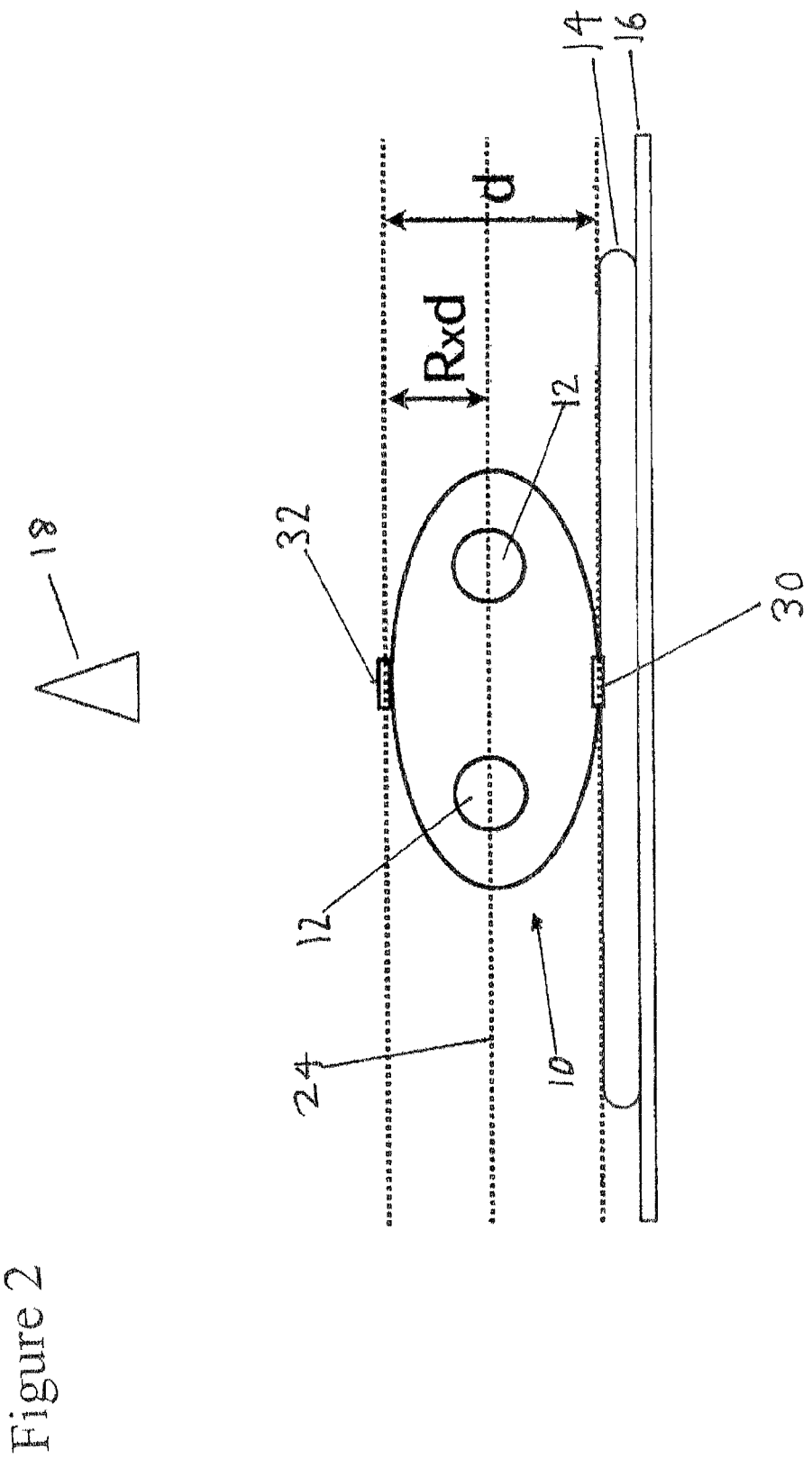
FIG. 2 shows a schematic diagram showing the arrangement used in the current invention.
Figure 3:
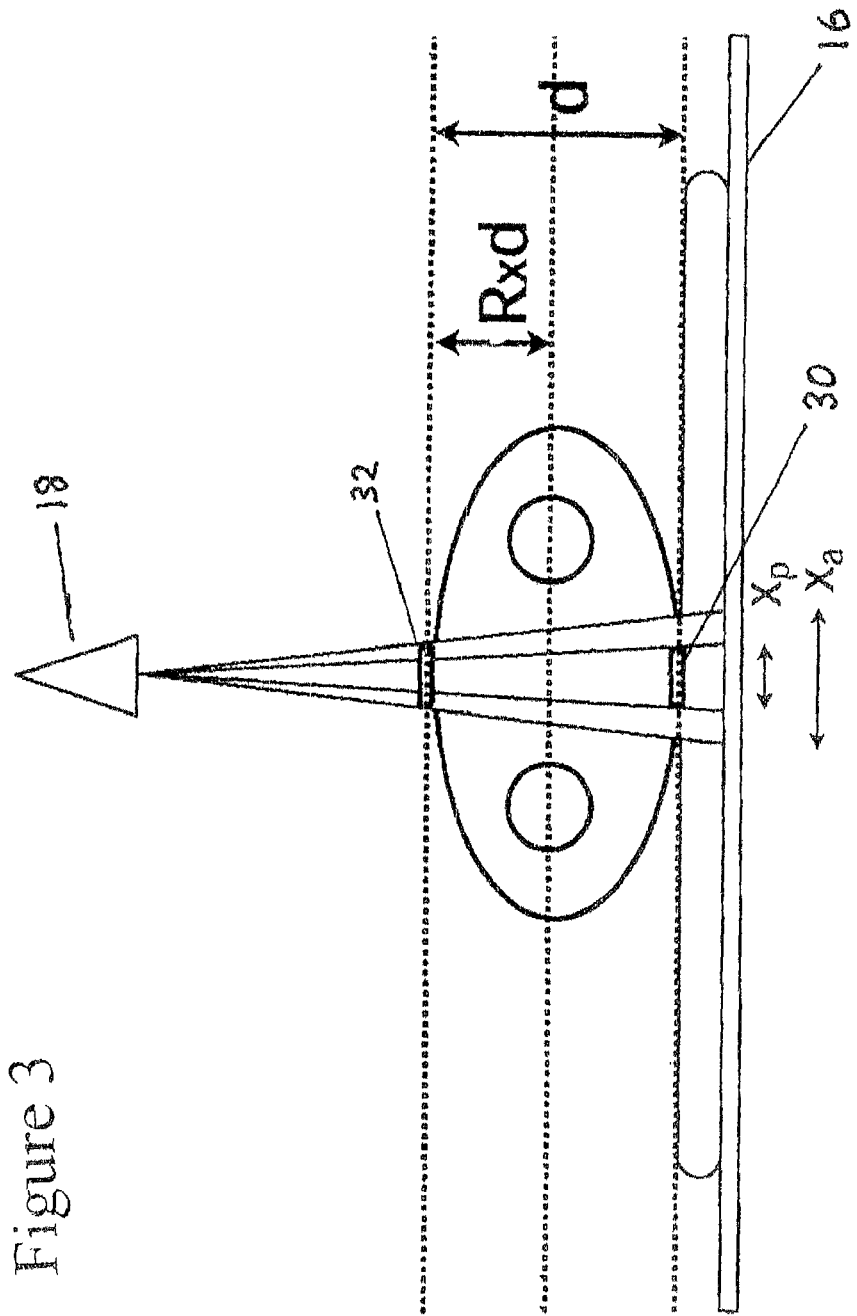
FIG. 3 shows the magnification of the image of the markers used according to the current invention.

FIGS. 1 to 3, as previously discussed, shows the prior art use of markers and the arrangement of the markers of the current invention. Measurement R, the distance between a line passing through centres of the hip sockets of patients to the surface of the patient's abdomen (where the anterior marker would be placed), in comparison to the distance between the back of the patient where a posterior marker might be placed to the abdomen of the patient, thus calculated using CT scans of patients. The value of R was calculated from 50 scans.

Figure 4:
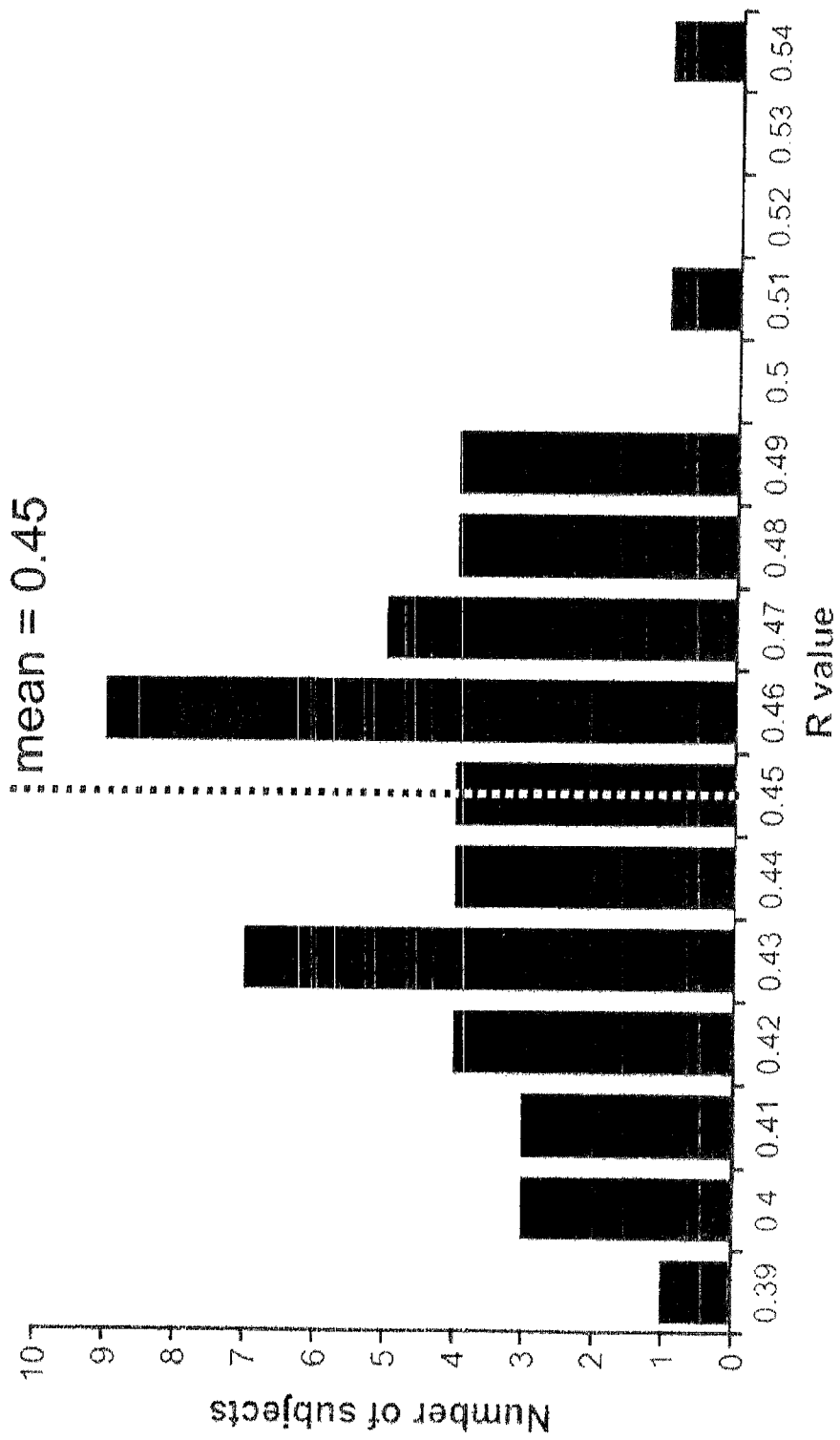
FIG. 4 shows a graph of the value of R, for 50 patients.

FIG. 4 shows the range of values obtained for R, the ratio between the two distances. The mean value of 0.45 was obtained. Prototype marker comprising a mat with 1" brackets (2.54 centimeters), rods recessed into it. An anterior marker comprising a strip of five 1" (2.54 centimeter) steel ball-bearings spaced apart but held together by a strip of material was also provided. The marker design was validated using pelvic x-rays of 74 hip prostheses.

Figure 5:
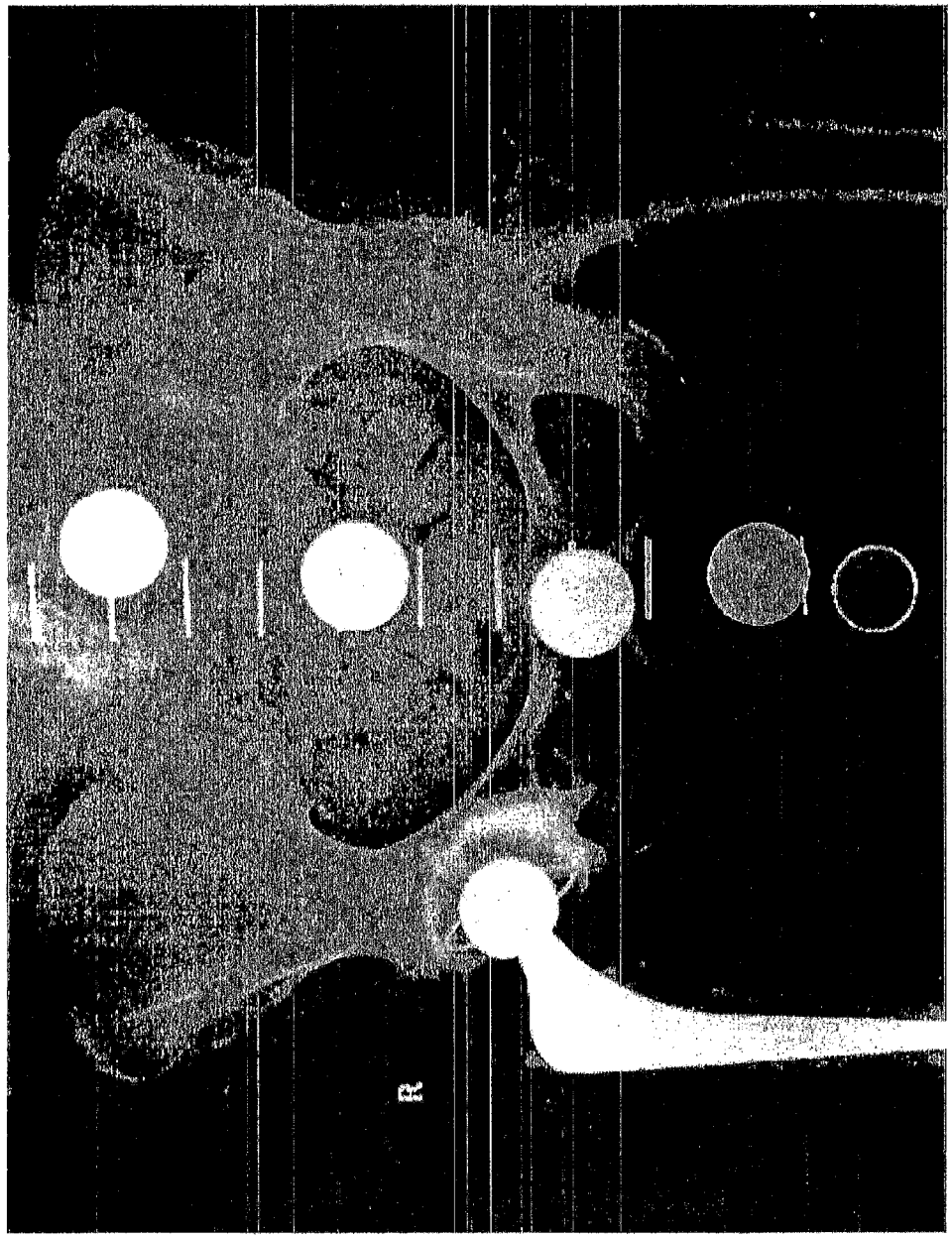
FIG. 5 shows an x-ray of a patient showing the anterior and posterior markers.

FIG. 5 shows a typical x-ray. The ball-bearings (the anterior marker) are represented by the solid white circles. The rods are indicated by the ladder like series of parallel lines also present on the image. The x-ray also clearly shows a replacement hip in the hip socket of a patient.

74 patients analysed comprise 28 male and 46 female with a BMI (body mass index) averaging 28.8 (with a range of 17.4-45.8). Several prostheses where measured, including a THR head, a CORMET head and a PINNACLE cup.

Patients were laid upon the mat and the strip of balls simply placed on the surface of the abdomen. The placement of the patient and balls proved to be very simple and easy for the radiographer. It did not require the accurate positioning of previously known markers.

Figure 6:
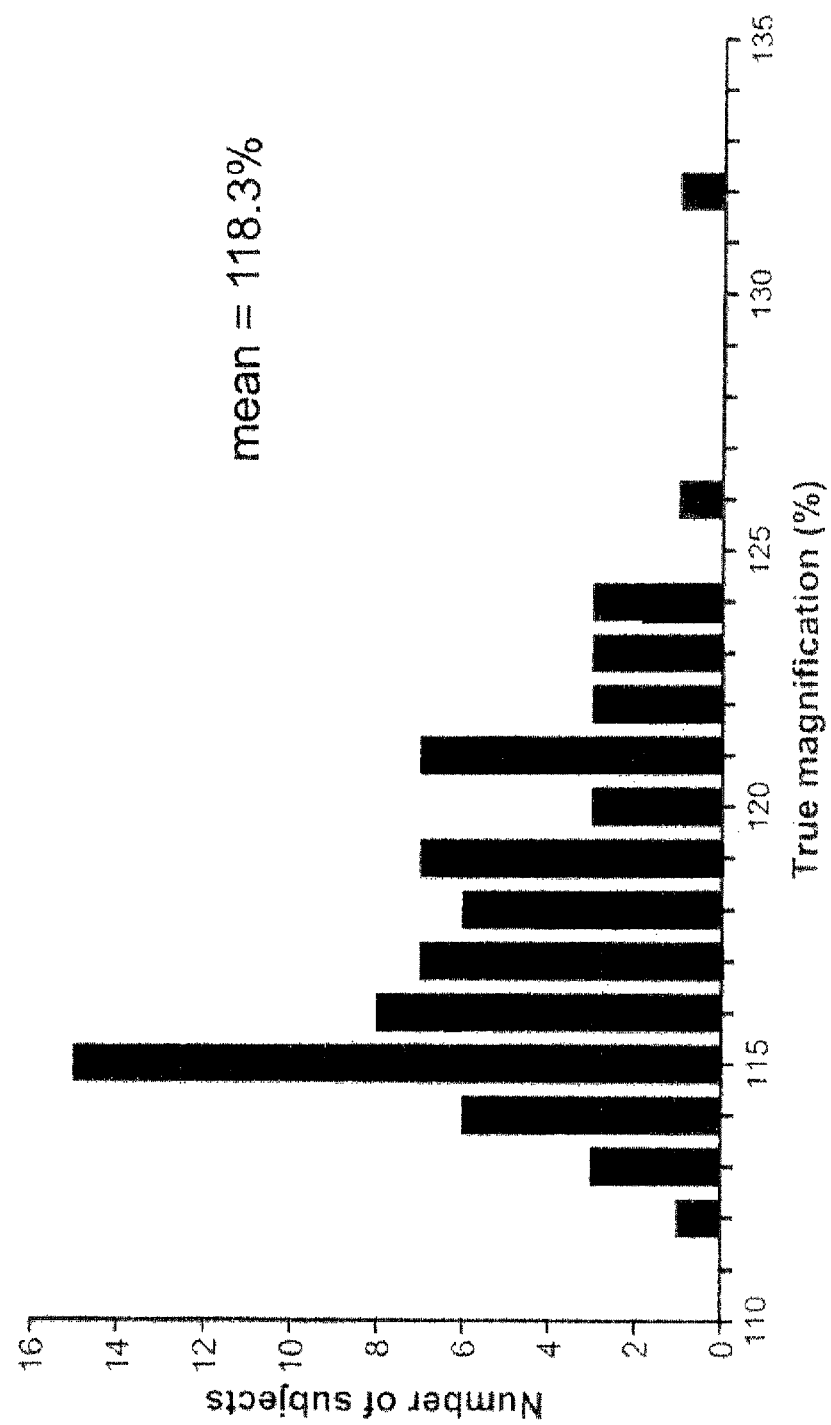
FIG. 6 shows a graph showing the true magnification of a pelvic x-ray of 74 patients.

FIG. 6 shows the true magnification of the 74 patients used in the images of the hips in the sample. The accuracy of the magnification of the marking technique of the current invention was compared to that provided by a previously known marker. Currently the known marker utilises a radioopaque ball on the end of a flexible arm which holds the ball in position compared to the patient.

Figure 7:
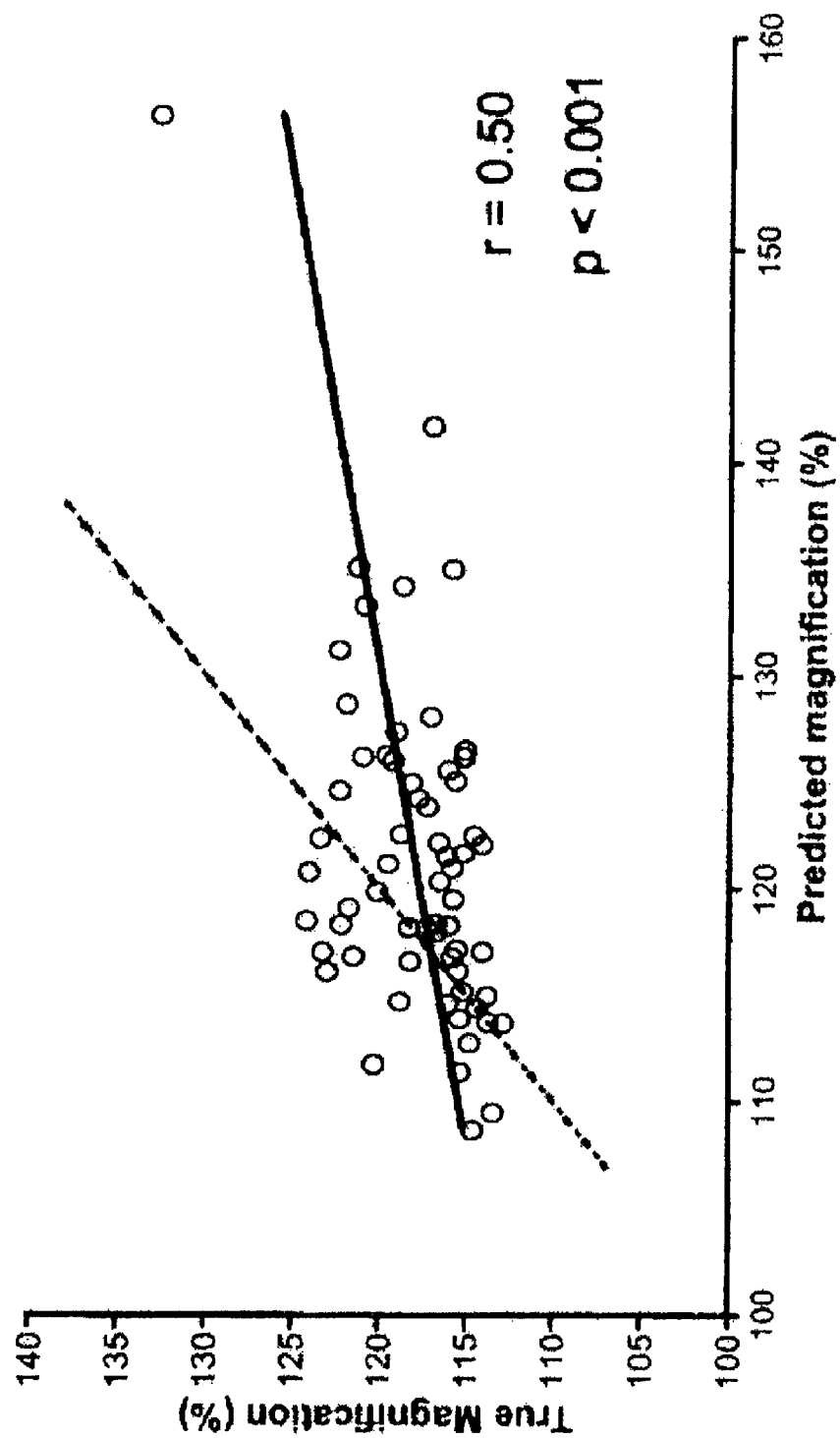
FIG. 7 shows magnification of pelvic images predicted by a prior art marker compared to a line representing 100% accurate calculation.

FIG. 7 shows the predicted magnification of the currently used marker. The two lines represent the magnification of the ideal marker, providing 100% accuracy, compared to the predicted magnification using the current marker. This clearly shows that the current marker is inaccurate.

The relative dimensions of the anterior and posterior markers of the current invention were also calculated and the magnification calculated according to the formula:

$$M = \frac{100}{\left[\frac{S_a}{X_a}\right] + R\left[\frac{S_p}{X_p} - \frac{S_a}{X_a}\right]}$$

where,
M is the magnification,
$S_a$ is the actual dimension of the anterior marker,
$S_p$ is the actual dimension of the posterior marker,
$X_a$ is the apparent dimension of the anterior marker recorded on the image,
$X_p$ is the apparent dimension of the posterior marker recorded on the image and
R is the pre-determined value.

Figure 8:
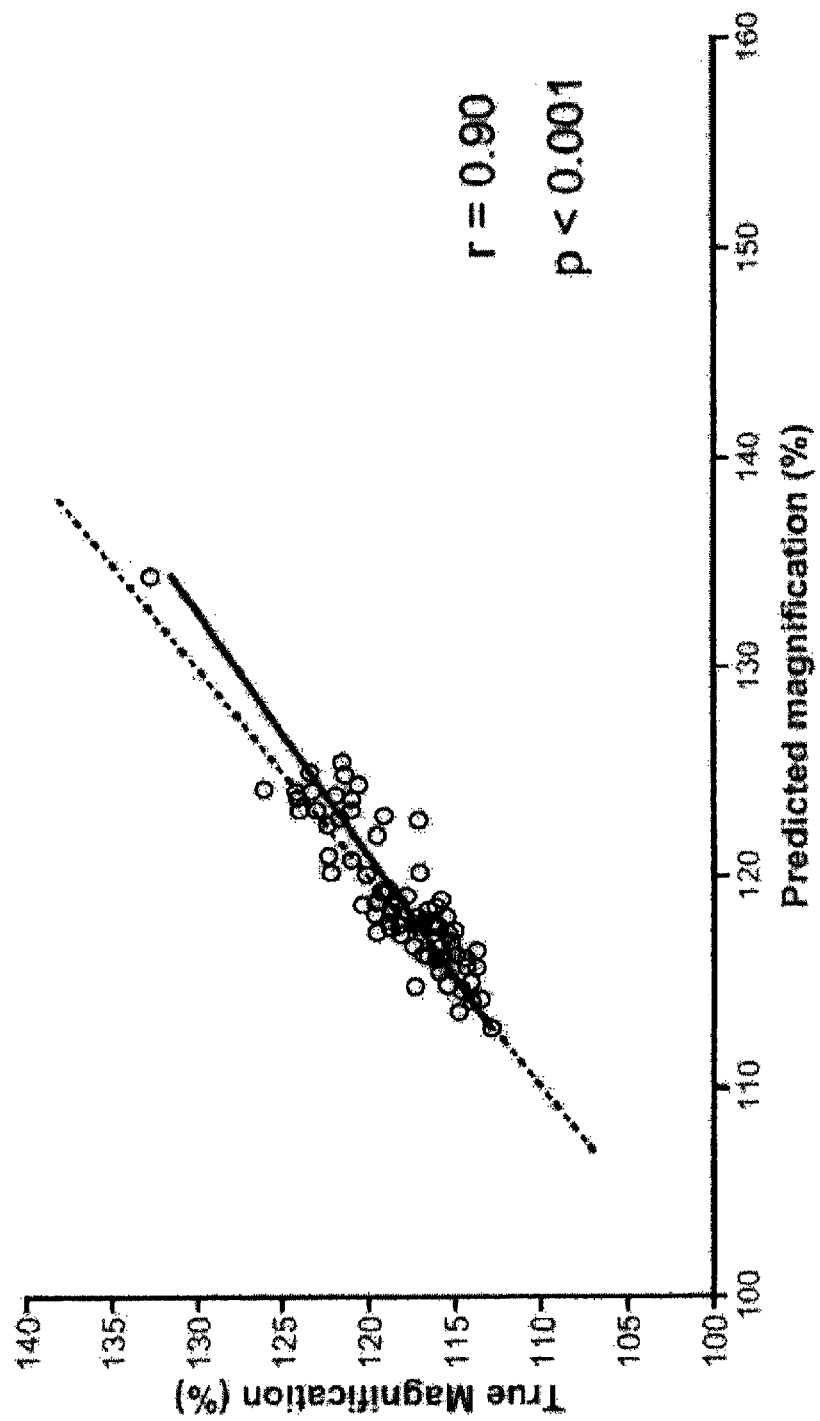
FIG. 8 shows magnification of pelvic images calculated by the method of the invention. The two lines represent 100% accurate calculation against the practical magnification.

The predicted magnification is shown in FIG. 8. The two lines represent the predicted magnification using the new marker with the ideal marker. This clearly demonstrates a vast improvement of the accuracy of the marker compared to the prior art marker.

Figure 9:
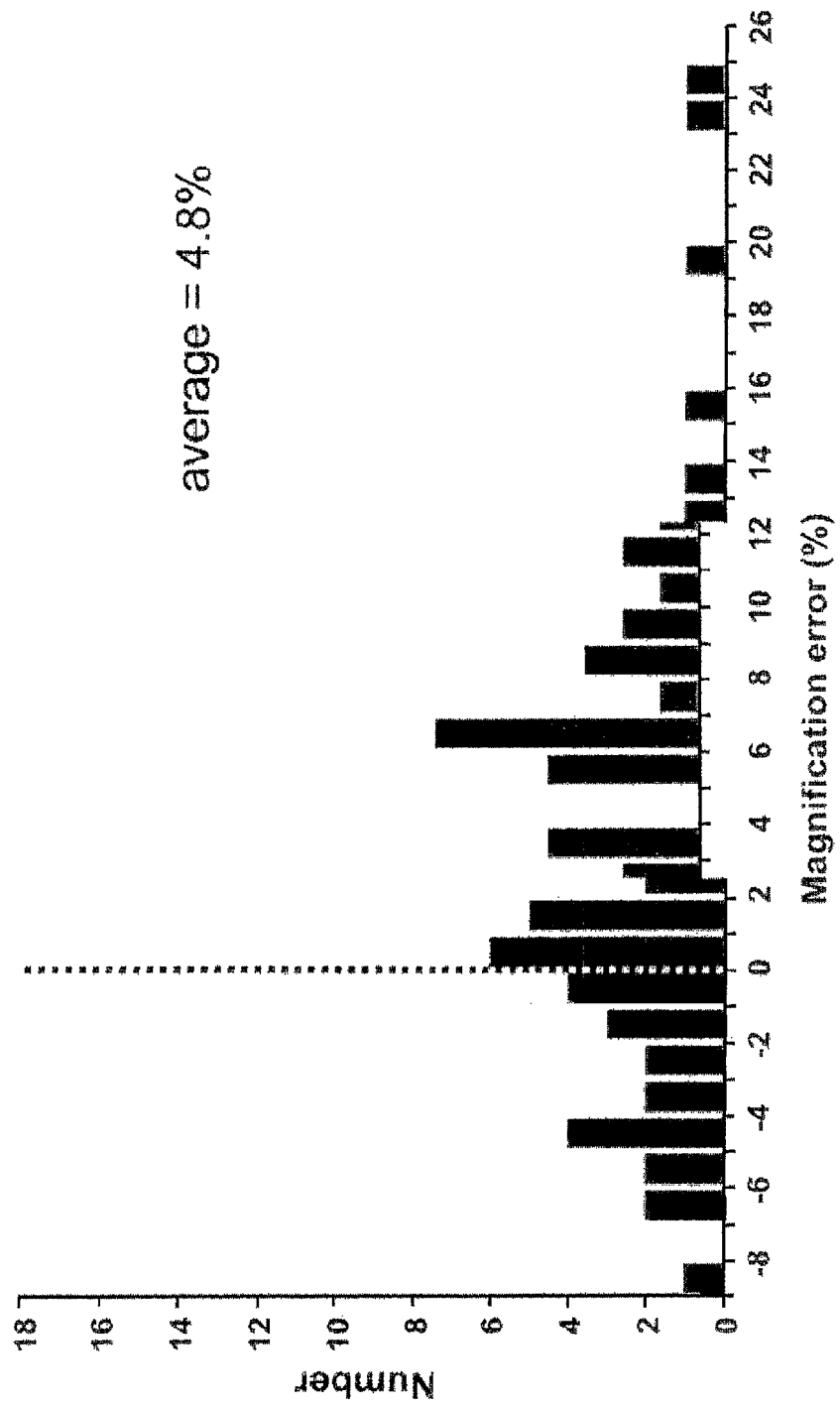
FIG. 9 shows magnification errors of prior art markers.
Figure 10:
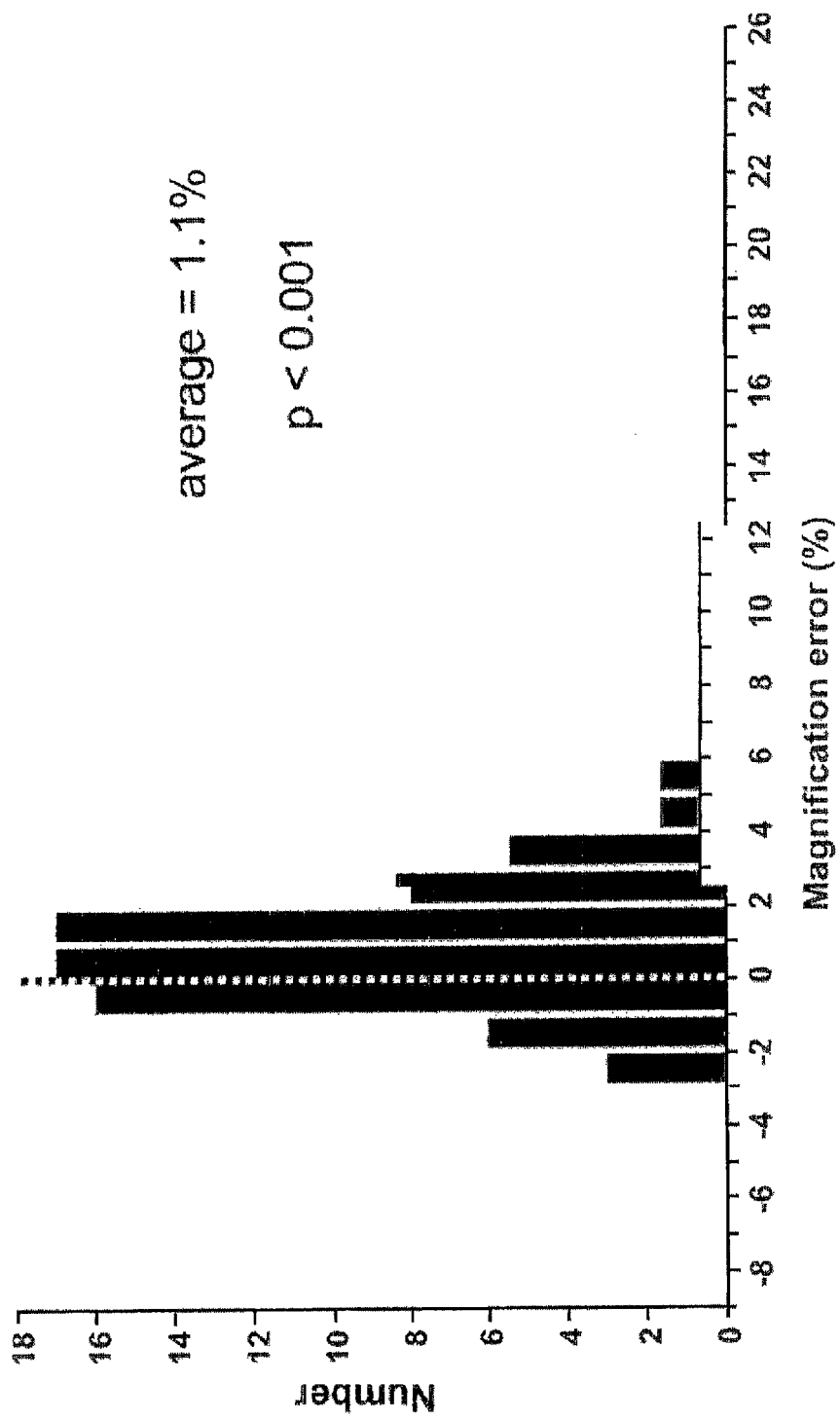
FIG. 10 shows magnification errors of method of the invention.
Figure 11:
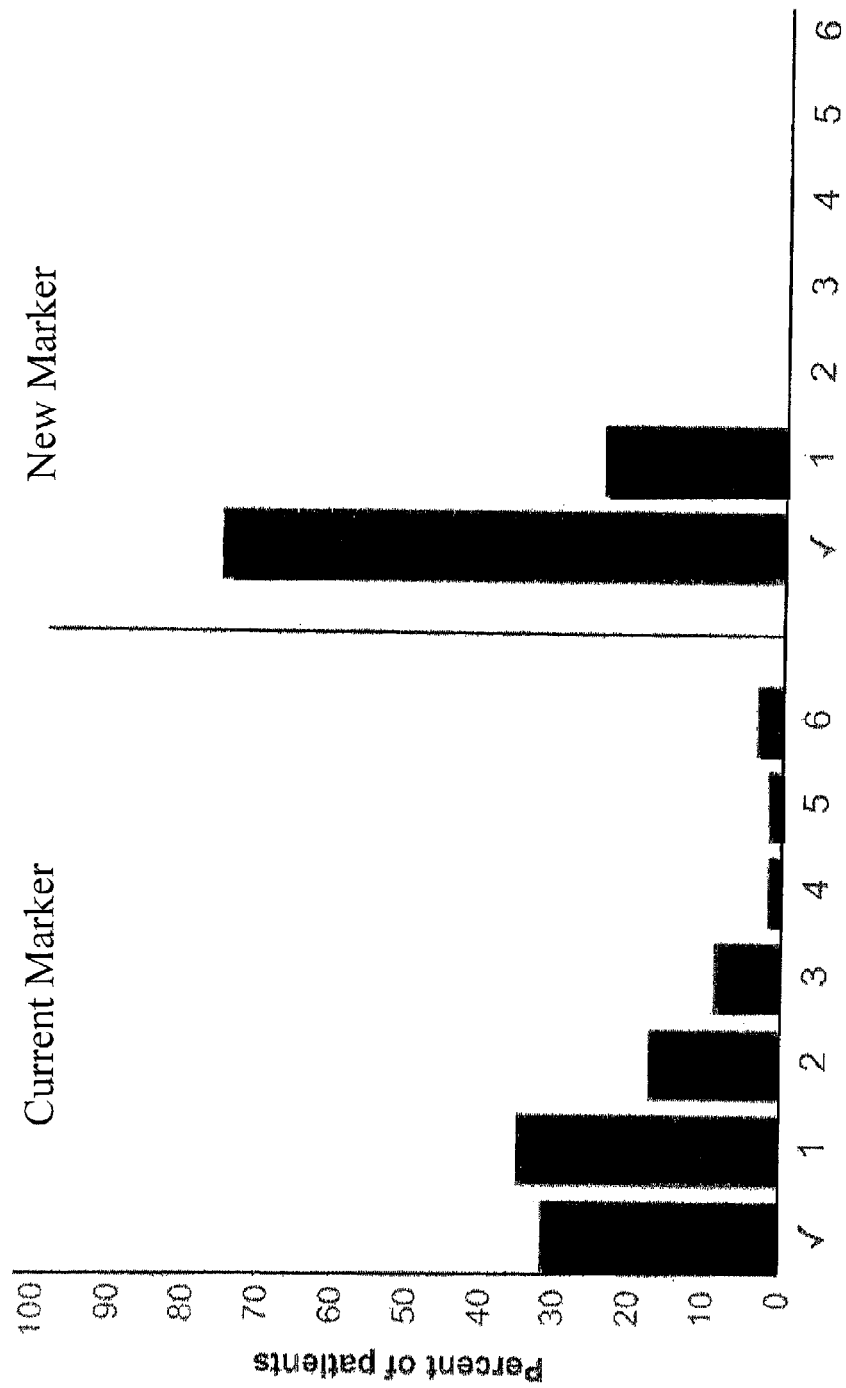
FIG. 11 shows comparison of the cup sizes estimated for a hip replacement for the prior art method compared to the new marker method of the invention for a 50 mm cup.

FIGS. 9 and 10 show the magnification errors for the prior art marker compared to the marker of the current invention. Errors identified using the current invention are considerably reduced and the range of the errors is more limited. This has a very practical, direct result for the patient. Using the prior art marker, the range of errors could produce an estimated cup diameter for hip replacement, for a 50 mm cup, of up to six sizes difference. However, for the new marker more of the cup sizes will be accurately determined and those that are not accurately determined are likely to fall within only one cup size difference. This has considerable benefits in that it allows a correct fitting of the correct hip replacement size and reduces the likelihood that the correct sized hip replacements are not available for a patient. This is shown in FIG. 11.

By way of a comparison, the inventors also compared body mass index versus the true magnification observed. They observed that magnification is poorly related to body mass index. Hence, simply using body mass index as a way of obtaining magnification would not be accurate.

In conclusion, the currently claimed invention has been observed to greatly increase the accuracy of the calculation of the magnification of x-rays. Moreover, the technique is simple and easy to carry out, without the need of the accurate positioning of a marker. The technique can be readily applied to other types of x-ray, and is not limited to the x-rays of hips.

The invention claimed is:

1. A method of determining the magnification of an x-ray image of an object, or a portion of an object, the method comprising the steps of:
   (i) providing an object to be x-rayed;
   (ii) providing a first posterior x-ray marker having a pre-determined dimension;
   (iii) providing anteriorly to the object to be x-rayed, a second x-ray marker having predetermined dimensions;
   (iv) recording an x-ray image of the object, the first posterior x-ray marker, and second x-ray markers; and
   (v) comparing a dimension of the first posterior x-ray marker recorded on the x-ray image, and a dimension of the second x-ray marker recorded on the image to a pre-determined value for the object x-rayed, to estimate a magnification of the x-ray image of the object.

2. A method according to claim 1, wherein the object is selected from a group consisting of a human patient and an animal patient.

3. A method according to claim 1, wherein the first x-ray marker is provided substantially adjacent to an x-ray detector.

4. A method according to claim 1, wherein the second x-ray marker is placed on a surface of the object anteriorly to an x-ray source.

5. A method according to claim 2, wherein a portion of the object is selected from a group consisting of a hip joint, a knee joint, a shoulder joint, an elbow and a portion of a spine.

6. A method according to claim 5, wherein the portion of the object x-rayed is a human hip joint and the predetermined value is the typical distance between a line passing through the centers of both hip joints to the position of the anterior second x-ray marker on the surface of an abdomen, compared to the distance between the anterior second x-ray marker and the first posterior x-ray marker.

7. A method according to claim 1, wherein the magnification of the image is determined according to the following equation $$M = \frac{100}{\left[\frac{S_a}{X_a}\right] + R\left[\frac{S_p}{X_p} - \frac{S_a}{X_a}\right]}$$

$S_a$=a dimension of the second x-ray marker,
$S_p$=a dimension of the first posterior x-ray marker,
$X_a$=the dimension of the second x-ray marker recorded on the image,
$X_p$=the dimension of the first posterior x-ray marker recorded on the image,
R=the pre-determined value for the object,
M=magnification of the image.

8. A method according to claim 1, wherein the first posterior x-ray marker is one more first posterior x-ray markers selected from a group consisting of rods, discs, washers, wires, and balls.

9. A method according to claim 1, wherein the dimension is selected from the group consisting of a length of a rod, a diameter of a ball, a diameter of washer or a diameter of disc, and the distance between two parallel rods or wires.

10. A method according to claim 1, wherein the object is placed on a mat adjacent to an x-ray detector, and the mat comprises one or more markers.

11. A method according to claim 1, wherein the anterior second x-ray marker is one or more anterior second x-ray markers selected from a group consisting of balls, washers and discs.

12. A method according to claim 1, wherein the estimation of the magnification of an x-ray image is conducted using the following equation:

$$M = \frac{100}{\left[\frac{S_a}{X_a}\right] + R\left[\frac{S_p}{X_p} - \frac{S_a}{X_a}\right]}$$

$S_a$=a dimension of the second x-ray marker,
$S_p$=a dimension of the first posterior x-ray marker,
$X_a$=the dimension of the second x-ray marker recorded on the image,
$X_p$=the dimension of the first posterior x-ray marker recorded on the image,
R=the pre-determined value for the object,
M=magnification of the image.

13. A kit for use in a method according to claim 1, the kit comprising a mat comprising one or more markers, the one or more markers having a pre-determined dimension and capable of being detected by x-ray imaging.

14. A kit according to claim 13, wherein the one or more markers are selected from a group consisting of discs, washers, rods, and wires.

15. A kit according to claim 13, additionally comprising a first marker, the first marker is one or more first markers selected from a group consisting of ball-bearings, washers, and discs for placing on an anterior surface of an object to be x-rayed.

16. A kit according to claim 15, further comprising a plurality of second markers selected from a group consisting of ball-bearings, discs and washers, wherein the plurality of second markers are linked together via one or more strips of flexible material.

17. A system for determining the magnification of an x-ray image of an object comprising a processor and a memory, the memory comprising an image, the image comprising an image of a first x-ray marker, an image of a second x-ray marker and an image of an object or part of an object; the processor configured to:
   (i) place a cursor over the image of the first x-ray marker and calculate a dimension of the first x-ray marker;
   (ii) place a cursor over the image of the second x-ray marker and calculate a dimension of the second x-ray marker; and
   (iii) compare the two dimensions with a pre-determined value for the object, or part of the object, of the image to provide an estimate of the magnification of the image.

18. The system of claim 17, wherein the system is operable to:
   (i) provide an object to be x-rayed;
   (ii) provide a first posterior x-ray marker having a pre-determined dimension;
   (iii) provide anteriorly to the object to be x-rayed, a second x-ray marker having predetermined dimensions;

(iv) record an x-ray image of the object, the first posterior x-ray marker, and second x-ray markers; and (v) compare a dimension of the first x-ray marker recorded on the x-ray image, and a dimension of the second x-ray marker recorded on the image to a pre-determined value for the object x-rayed, to estimate a magnification of the x-ray image of the object.

19. The method of claim 17, wherein the estimate of the magnification of the image is conducted using the following equation:

$$M = \frac{100}{\left[\frac{S_a}{X_a}\right] + R\left[\frac{S_p}{X_p} - \frac{S_a}{X_a}\right]}$$

$S_a$=a dimension of the anterior marker,
$S_p$=a dimension of the posterior marker,
$X_a$=the dimension of the anterior marker recorded in the image,
$X_p$=the dimension of the posterior marker recorded on the image,
R=the pre-determined value for the object,
M=Magnification of the image.

20. An x-ray device comprising:

an x-ray source;

an x-ray detector; and a mat comprising one or more markers, the mat arranged to be placed adjacent to the x-ray detector; and one or more markers for placing on an anterior surface of an object to be x-rayed;

wherein the one or more markers have a pre-determined dimension and are capable of being detected by x-ray imaging.

\* \* \* \* \*